(12) United States Patent
Dickerson et al.

(10) Patent No.: US 10,426,506 B2
(45) Date of Patent: Oct. 1, 2019

(54) ULTRASONIC SURGICAL INSTRUMENT WITH MULTI-GRIP ACTIVATION AND POWER SELECTION

(71) Applicant: Ethicon Endo-Surgery, LLC, Guaynabo, PR (US)

(72) Inventors: Benjamin D. Dickerson, Cincinnati, OH (US); Tylor C. Muhlenkamp, Cincinnati, OH (US); Paul F. Riestenberg, North Bend, OH (US); Kristen G. Denzinger, Cincinnati, OH (US); Craig N. Faller, Batavia, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 815 days.

(21) Appl. No.: 14/836,270

(22) Filed: Aug. 26, 2015

(65) Prior Publication Data

US 2017/0056053 A1    Mar. 2, 2017

(51) Int. Cl.
*A61B 17/32*   (2006.01)
*A61B 17/29*   (2006.01)
*A61B 17/00*   (2006.01)

(52) U.S. Cl.
CPC .......... *A61B 17/320068* (2013.01); *A61B 2017/00367* (2013.01); *A61B 2017/00389* (2013.01); *A61B 2017/2918* (2013.01)

(58) Field of Classification Search
CPC .. A61B 17/320068; A61B 2017/00367; A61B 2017/320069
See application file for complete search history.

(56) References Cited

U.S. PATENT DOCUMENTS 4,608,978 A * 9/1986 Rohr ............... A61B 18/203
                                                    606/11
5,322,055 A    6/1994 Davison et al.
(Continued)

FOREIGN PATENT DOCUMENTS

DE          24 60 481 A1    6/1976
WO    WO 2008/089174 A2    7/2008

OTHER PUBLICATIONS

U.S. Appl. No. 61/410,603, filed Nov. 5, 2010.
International Search Report and Written Opinion dated Sep. 29, 2016 for Application No. PCT/US2016/047154, 13 pgs.

*Primary Examiner* — Diane D Yabut
*Assistant Examiner* — Majid Jamialahmadi
(74) *Attorney, Agent, or Firm* — Frost Brown Todd LLC

(57) ABSTRACT

An ultrasonic instrument for use during a surgical procedure includes a body, a shaft assembly, an ultrasonic blade, and an actuation assembly. The body is configured to receive an ultrasonic transducer for selectively generating an oscillation at a first or a second predetermined power level. The shaft assembly projects from the body and includes an acoustic waveguide connected to the ultrasonic blade. The actuation assembly includes a selector collar generally surrounding the body and a plurality of activation buttons disposed radially about the body proximate to the selector collar. The selector collar is selectively movable along the body between a first position and a second position for selecting between the first and second predetermined power levels. The plurality of activation buttons are configured to direct the ultrasonic blade to oscillate with the selected first or second predetermined power levels.

18 Claims, 7 Drawing Sheets

(56) References Cited

U.S. PATENT DOCUMENTS

| | | |
|---|---|---|
| 5,324,299 A | 6/1994 | Davison et al. |
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 6,945,981 B2 | 9/2005 | Donofrio et al. |
| 8,057,498 B2 | 11/2011 | Robertson |
| 8,152,825 B2 | 4/2012 | Madan et al. |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0069940 A1* | 3/2010 | Miller ............... A61B 17/32006 606/169 |
| 2012/0116265 A1 | 5/2012 | Houser et al. |
| 2013/0245704 A1* | 9/2013 | Koltz .................... A61B 17/00 606/86 A |
| 2015/0080924 A1 | 3/2015 | Stulen et al. |
| 2015/0148829 A1* | 5/2015 | Kimball ........... A61B 17/32006 606/169 |
| 2015/0148830 A1 | 5/2015 | Stulen et al. |
| 2016/0022305 A1 | 1/2016 | Lamping et al. |
| 2016/0074060 A1 | 3/2016 | Messerly et al. |
| 2016/0106455 A1 | 4/2016 | Aldridge et al. |

* cited by examiner

ULTRASONIC SURGICAL INSTRUMENT WITH MULTI-GRIP ACTIVATION AND POWER SELECTION

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
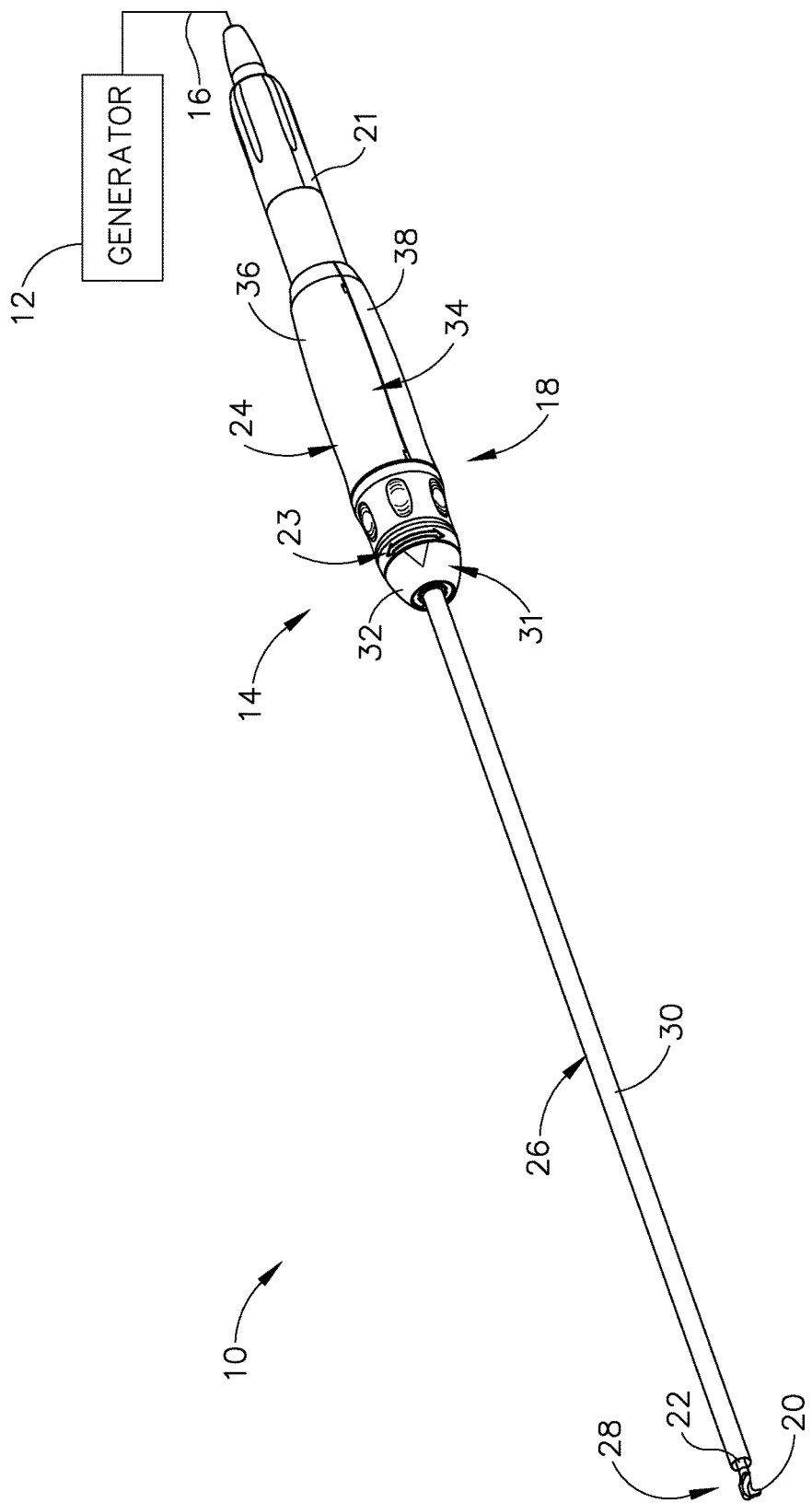
FIG. 1 depicts a perspective view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10). As shown, the surgical system (10) comprises an ultrasonic generator (12) and an ultrasonic surgical instrument (14). As will be described in greater detail below, the surgical instrument (14) is operable to cut tissue and seal or weld tissue (e.g., a blood vessel, etc.) substantially simultaneously, using ultrasonic vibrational energy. The generator (12) and the surgical instrument (14) are coupled together via a cable (16). The cable (16) may comprise a plurality of wires; and may provide unidirectional electrical communication from the generator (12) to the surgical instrument (14) and/or bidirectional electrical communication between the generator (12) and the surgical instrument (14). By way of example only, the cable (16) may comprise a "hot" wire for electrical power to the surgical instrument (14), a ground wire, and a signal wire for transmitting signals from the surgical instrument (14) to the ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of the surgical system (10) may incorporate the generator (12) into the surgical instrument (14), such that the cable (16) may simply be omitted.

By way of example only, the ultrasonic generator (12) may comprise the GEN04, GEN11, or GEN 300 sold by Ethicon Endo-Surgery, Inc. of Cincinnati, Ohio. In addition or in the alternative, the ultrasonic generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generators may be used. As will be described in greater detail below, the ultrasonic generator (12) is operable to provide power to the surgical instrument (14) to perform ultrasonic surgical procedures.

The surgical instrument (14) comprises a handpiece (18), which is configured to be grasped in one hand (or two hands) of an operator and manipulated by one hand (or two hands) of the operator during a surgical procedure. For instance, in some versions, the handpiece (18) may be grasped like a pencil by the operator. In some other versions, the handpiece (18) may include a scissor grip that may be grasped like scissors by the operator. In some other versions, the handpiece (18) may include a pistol grip that may be grasped like a pistol by the operator. Of course, the handpiece (18) may be configured to be gripped in any other suitable fashion. Furthermore, some versions of the surgical instrument (14) may substitute the handpiece (18) with an alternative body (not shown) coupled to a robotic surgical system (not shown) configured to operate an alternative instrument, such as by remote control. In the present example, a blade (20) extends distally from the handpiece (18). The handpiece (18) includes an ultrasonic transducer (21) and an ultrasonic waveguide (22), which couples the ultrasonic transducer (21) with the blade (20). The ultrasonic transducer (21) receives electrical power from the generator (12) via the cable (14) and, by virtue of its piezoelectric properties, the ultrasonic transducer (21) converts such electrical power into ultrasonic vibrational energy. When the ultrasonic transducer (21) of the present example is activated, these mechanical oscillations are transmitted through the waveguide (22) to reach the blade (20), thereby providing oscillation of the blade (20) at the resonant ultrasonic frequency. Thus, the ultrasonic oscillation of the blade (20) may simultaneously sever the tissue and denature the proteins in adjacent tissue cells, thereby providing a coagulative effect with relatively little thermal spread. In some versions, an electrical current may also be provided through the blade (20) to also cauterize the tissue.

By way of example only, the ultrasonic waveguide (22) and the blade (20) may comprise components sold under product codes SNGHK and SNGCB by Ethicon Endo- Surgery, Inc. of Cincinnati, Ohio. By way of further example only, the ultrasonic waveguide (22) and/or the blade (20) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the ultrasonic waveguide (22) and/or the blade (20) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of the ultrasonic waveguide (22) and the blade (20) will be apparent to those of ordinary skill in the art in view of the teachings herein.

The handpiece (18) of the present example also includes an actuation assembly (23) in communication with a circuit board (not shown). By way of example only, the circuit board (not shown) may comprise a conventional printed circuit board, a flex circuit, a rigid-flex circuit, or may have any other suitable configuration. The actuation assembly (23) may be in communication with the circuit board (not shown) via one or more wires, traces formed in a circuit board or flex circuit, and/or in any other suitable fashion. The actuation assembly (23) is operable to selectively direct power from the generator (12) to the ultrasonic transducer (21) for operating the blade (20).

In the present example, the surgical system (10) is operable to provide at least two different levels or types of ultrasonic energy (e.g., different frequencies and/or amplitudes, etc.) at the blade (20). To that end, the actuation assembly (23) is operable to permit the operator to select a desired, predetermined power level for ultrasonic oscillation of the blade (20).

It should be understood that the ultrasonic oscillations provided at the blade (20) may be a function of characteristics of the electrical power communicated from the generator (12) to the surgical instrument (14) via the cable (16). Thus, control circuitry of the generator (12) may provide electrical power (via cable (16)) having characteristics associated with the ultrasonic energy level/amplitude or type selected through the actuation assembly (23). The generator (12) may thus be operable to communicate different types or degrees of electrical power to the ultrasonic transducer (21), in accordance with selections made by the operator via the actuation assembly (23). In particular, and by way of example only, the generator (12) may increase the voltage and/or current of the applied signal to increase the longitudinal amplitude of the acoustic assembly. As a merely illustrative example, the generator (12) may provide selectability between a maximum level and a minimum level, which may correspond with a blade vibrational resonance amplitude of approximately 50 microns and approximately 90 microns, respectively. Of course, it will be appreciated that other levels between and/or beyond maximum and minimum may be incorporated into the surgical instrument (18), as well.

In other examples, control circuitry (not shown) is located within the handpiece (18). For instance, the generator (12) may only communicate one type of electrical power (e.g., just one voltage and/or current available) to the handpiece (18) such that the control circuitry (not shown) within the handpiece (18) is operable to modify the electrical power (e.g., the voltage of the electrical power), in accordance with selections made by the operator, before the electrical power reaches the ultrasonic transducer (21). Furthermore, the generator (12) may be incorporated into the handpiece (18) along with all other components of the surgical system (10). For instance, one or more batteries (not shown) or other portable sources of power may be provided in the handpiece (18). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for the surgical instrument (14). It should be understood that the various examples of the surgical instrument (14) described below may be readily incorporated into the surgical system (10), as described above, or alternative surgical systems. It should also be understood that the various components and operability of the surgical instrument (14) described above may be readily incorporated into the exemplary versions of the surgical instrument (14) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
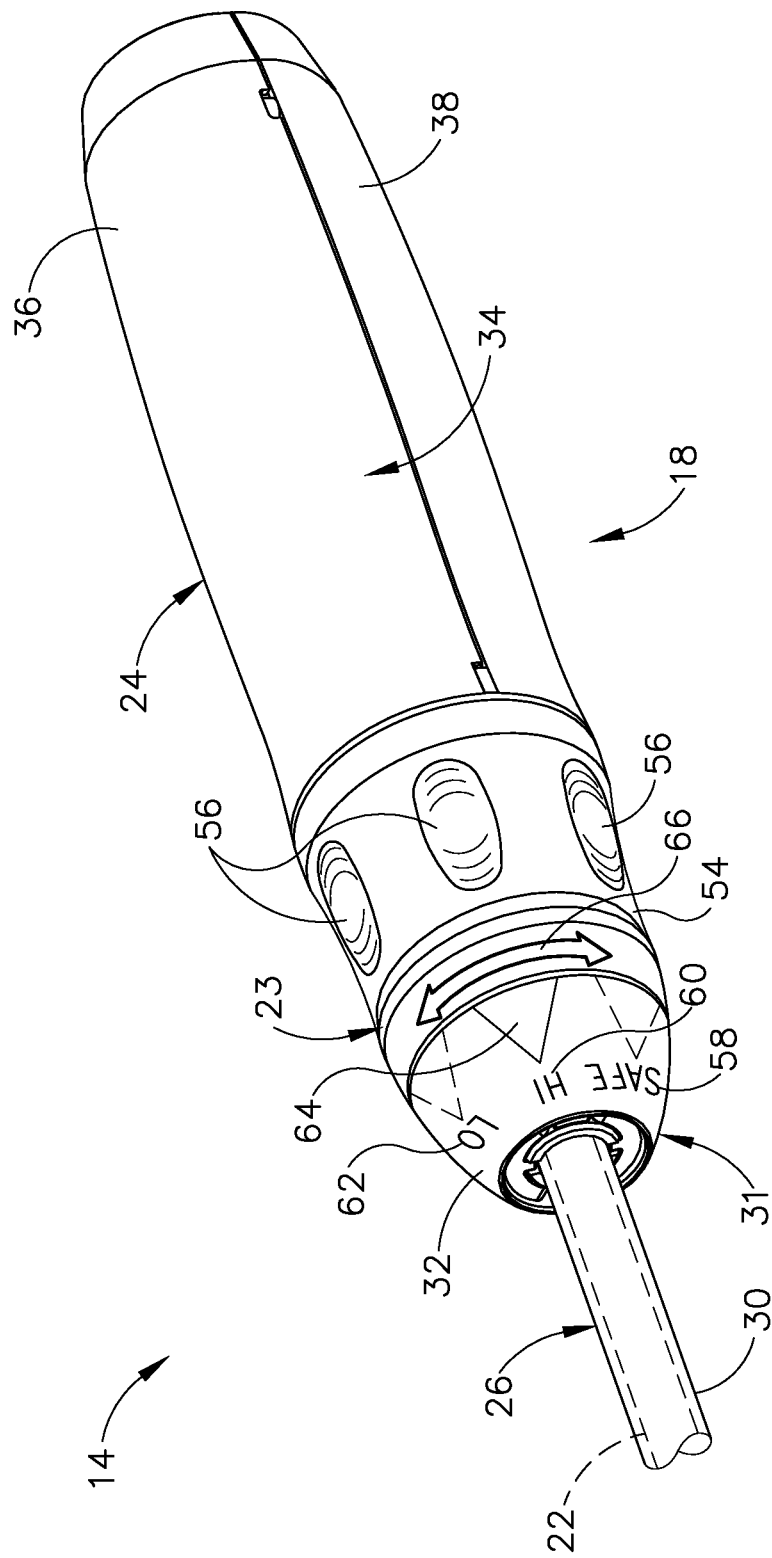
FIG. 2 depicts an enlarged perspective view of a handle assembly of the surgical instrument of FIG. 1.
Figure 3:
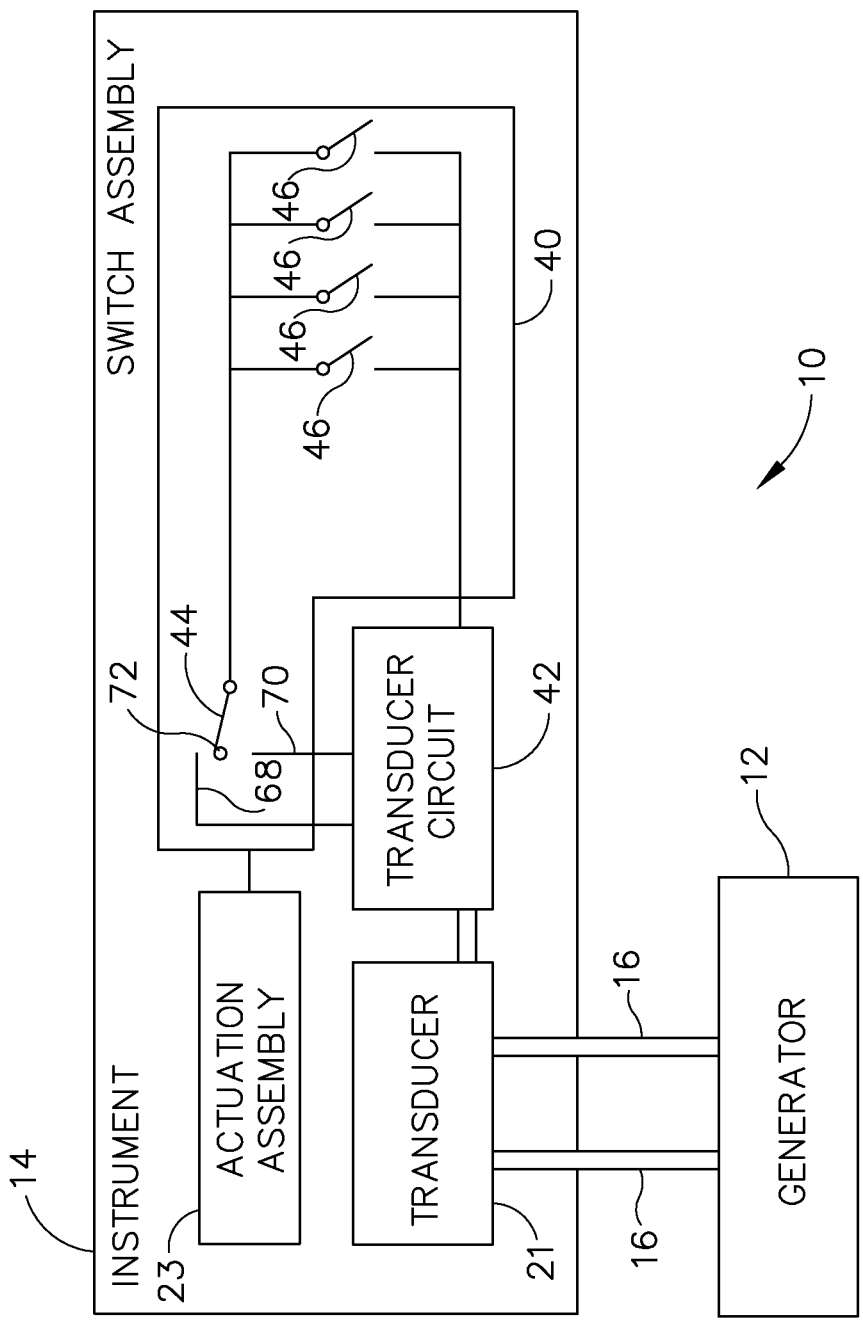
FIG. 3 depicts a schematic view of an exemplary electrical circuit of the surgical instrument of FIG. 1.

FIGS. 1-3 illustrate the exemplary ultrasonic surgical instrument (14). At least part of the surgical instrument (14) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, the surgical instrument (14) is operable to cut tissue and seal or weld tissue substantially simultaneously. It should also be understood that the surgical instrument (14) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the surgical instrument (14) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to the surgical instrument (14), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

The surgical instrument (14) is configured to be used as a scalpel. As shown in FIGS. 1-2, the surgical instrument (14) of this example comprises a handle assembly (24), a shaft assembly (26), an end effector (28), and the actuating assembly (23). In the present example, a proximal end of the surgical instrument (14) operatively connects to the ultrasonic transducer (21) by insertion of the ultrasonic transducer (21) into the handle assembly (24). The handle assembly (24) receives the ultrasonic transducer (21) such that the ultrasonic transducer (21) couples to the waveguide (22) in the shaft assembly (26) by a threaded connection, though any other suitable connection for such coupling may be used. As shown in FIGS. 1-2, the surgical instrument (14) may be coupled with the ultrasonic transducer (12) to form a single unit.

A. Exemplary Shaft Assembly and End Effector

As best seen in FIGS. 1-2, the shaft assembly (26) comprises an outer sheath (30) with the waveguide (22) disposed within the outer sheath (30). In some versions, the outer sheath (30) and the waveguide (22) are sized to fit through a trocar or other minimally invasive access port, such that the surgical instrument (14) may be used in a minimally invasive surgical procedure. The waveguide (22) is configured to transmit ultrasonic vibrations from the ultrasonic transducer (21) to the blade (20). By way of example only, the shaft assembly (26), the end effector (28), and the waveguide (22) may be constructed in accordance with at least some of the teachings of U.S. patent application Ser. No. 14/337,508, entitled "Ultrasonic Blade Overmold," filed Jul. 22, 2014, issued as U.S. Pat. No. 9,750,521 on Sep. 5, 2017, the disclosure of which is incorporated by reference herein.

The surgical instrument (14) lacks a clamp arm in this example, such that surgical instrument (14) is configured for use as an ultrasonic scalpel for simultaneously slicing and cauterizing tissue. Instead, the end effector (28) merely consists of the blade (20) that may be used for simultaneously slicing and cauterizing tissue. In some alternative versions, including but not limited to those described below, the end effector (28) may include a clamp arm (not shown) that may be used to compress tissue against the blade (20) to assist in grasping, sealing, and/or cutting the tissue. Such a clamp arm (not shown) may be removably coupled to surgical instrument (14). By way of example only, the removable clamp arm (not shown) may be provided in accordance with at least some of the teachings of U.S. patent application Ser. No. 14/488,330, entitled "Ultrasonic Surgical Instrument with Removable Clamp Arm," filed Sep. 17, 2014, issued as U.S. Pat. No. 10,058,346 on Aug. 28, 2018, the disclosure of which is incorporated by reference herein. Alternatively, a clamp arm may be provided in any other suitable fashion.

B. Exemplary Handle Assembly

As best seen in FIGS. 1-2, the handle assembly (24) comprises a torquing mechanism (31), which includes a rotation knob (32), and a tubular elongate body (34). The torquing mechanism (31) is configured to limit the amount of torque that can be applied between the shaft assembly (26) and the ultrasonic transducer (21) and will be discussed below in additional detail. The elongate body (34) is configured to permit a user to grip the handle assembly (24) from a variety of positions, while the user operates the actuation assembly (23) of the handpiece (18) from these respective positions. The exemplary actuation assembly (23) will be discussed below in additional detail.

By way of example only, the handle assembly (24) may be shaped to be grasped and manipulated in a pencil-grip arrangement, in a screwdriver-grip arrangement, and/or in any other suitable fashion. The elongate body (34) of the present example comprises a pair of mating housing portions (36, 38), though it should be understood that the handle assembly (24) may alternatively comprise just a single housing component. The housing portions (36, 38) may be constructed from a durable plastic, such as polycarbonate or a liquid crystal polymer. It is also contemplated that the housing portions (36, 38) may alternatively be made from a variety of materials or combinations of materials, including but not limited to other plastics, ceramics, and/or metals, etc.

In the present example, the elongate body (34) of the handle assembly (24) includes a proximal end, a distal end, and a cavity (not shown) extending longitudinally therein. The cavity (not shown) is configured to accept at least a portion of the actuation assembly (23) and at least a portion of the ultrasonic transducer (21). To this end, one or more electrical contacts (not shown) of the ultrasonic transducer (21) operatively connect with the actuation assembly (23) to provide the operator with finger-activated controls on the surgical instrument (14). More particularly, the ultrasonic transducer (21) of the present example includes two conductive rings (not shown) that are securely disposed within the elongate body (34) of the ultrasonic transducer (21). By way of example only, such conductive rings and/or other features of the ultrasonic transducer (21) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

With respect to FIGS. 2-3, the cavity (not shown) also contains a switch assembly (40). The switch assembly (40) provides an electro-mechanical interface between the actuation assembly (23) and the generator (12) via the ultrasonic transducer (21) and an ultrasonic transducer circuit (42). The switch assembly (40) of the present example comprises a plurality of contact switches (44, 46) for selectively directing operation the surgical system (10) as will be discussed below in additional detail. Each of the contact switches (44, 46) respectively comprise an electrical contact switch in this example, such that the contact switches (44, 46) provide an electrical signal to the generator (12) and/or closes a circuit between the generator (12) and the ultrasonic transducer (21). By way of example only, various components of the switch assembly (40) may operatively connect to the ultrasonic transducer (21), such as by ring conductors (not shown) of the ultrasonic transducer (21). Thus, when one or more of the contact switches (44, 46) are actuated, the generator (12) activates the ultrasonic transducer (21) to generate ultrasonic vibrations. As described herein, the contact switches (44, 46) are more specifically referred to herein as a selector switch (44) and an activation switch (46).

As mentioned above, the ultrasonic transducer (21) threadably couples with the waveguide (22) of the shaft assembly (26) in this example. The proximal end of the shaft assembly (26) comprises the torquing mechanism (31) configured to permit coupling of the waveguide (22) with the ultrasonic transducer (21); while at the same time limiting the amount of torque that can be applied to the shaft assembly (26) and/or the ultrasonic transducer (21). By way of example, the torquing mechanism (31) comprises the rotation knob (32), an annular rack (not shown), and a wave spring (not shown). More particularly, the rotation knob (32) is rotatably disposed about the shaft assembly (26) such that the rotation knob (32) may be rotated about the shaft assembly (26).

During an initial stage of assembly of the surgical instrument (14), an operator may first align the ultrasonic transducer (21) along a longitudinal axis shared by the handle assembly (24) and the shaft assembly (26), then insert the ultrasonic transducer (21) into the proximal end of the handle assembly (24). The wave spring (not shown) will ensure initial contact between the distal end of the ultrasonic transducer (21) and the proximal end of the waveguide (22) as the ultrasonic transducer (21) is inserted into the handle assembly (24). The operator may then grasp the ultrasonic transducer (21) with one hand and grasp either the handle assembly (24) or the rotation knob (32) with the other hand. Once these components are firmly grasped, the operator may rotate the handle assembly (24) or the rotation knob (32) relative to the ultrasonic transducer (21) about the longitudinal axis. As such, the handle assembly (24), the rotation knob (32), and the shaft assembly (26) will all rotate together concurrently relative to the ultrasonic transducer (21).

As the handle assembly (24) and the shaft assembly (26) rotate relative to the ultrasonic transducer (21), the waveguide (22) is threaded onto the ultrasonic transducer (21) until the waveguide (22) encounters a predetermined resistance to further rotation. The predetermined resistance indicates that the ultrasonic transducer (21) and the waveguide (22) are operatively connected at a predetermined torque level. As such, the torquing assembly (31) is configured to act as a slip clutch and restrict the amount of torque by which the waveguide (22) may be coupled with the ultrasonic transducer (21).

It should be understood that the above described example of torquing mechanism (31) is merely illustrative. The torquing mechanism (31) may be constructed and operable in any other suitable fashion. By way of example only, the torquing mechanism (31) may be constructed and operable in accordance with at least some of the teachings of U.S. patent application Ser. No. 14/087,383, entitled "Features for Coupling Surgical Instrument Shaft Assembly with Instrument Body," filed on Nov. 22, 2013, issued as U.S. Pat. No. 10,368,892 on Aug. 6, 2019, the disclosure of which is incorporated by reference herein. Other suitable ways in which the torquing mechanism (31) may be constructed and operable will be apparent to those of ordinary skill in the art in view of the teachings herein.

The surgical instrument (14) may further be configured and operable in accordance with the teachings of U.S. Pub. No. 2008/0200940, entitled "Ultrasonic Energy Device for Cutting and Coagulating," published Aug. 21, 2008, now abandoned, the disclosure of which is incorporated by reference herein. Alternatively, the surgical instrument (14) may be provided with a variety of other components, configurations, and/or types of operability as will be apparent to those of ordinary skill in the art in view of the teachings herein.

In addition to or in lieu of being constructed in accordance with the above teachings, at least part of the surgical instrument (14) may be constructed and operable in accordance with at least some of the teachings of U.S. Pat. Nos. 5,322,055; 5,873,873; 5,980,510; 6,283,981; 6,309,400; 6,325,811; 6,423,082; 6,783,524; 8,057,498; 8,461,744; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2008/0234710, issued as U.S. Pat. No. 8,911,460 on Dec. 16, 2014; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pat. App. No. 61/410,603. The disclosures of each of the foregoing patents, publications, and applications are incorporated by reference herein. Additional merely illustrative variations for the surgical instrument (14) will be apparent to those of ordinary skill in the art in view of the teachings herein. It should be understood that the below described variations may be readily applied to the surgical instrument (14) described above and any of the instruments referred to in any of the references that are cited herein, among others.

C. Exemplary Actuation Assembly

FIGS. 2-3 show one example of the actuation assembly (23) that connects with the switch assembly (40) for both selecting between at least two predetermined ultrasonic power settings and activating the surgical instrument (14) accordingly. The actuation assembly (23) includes a selector element in the form of a selector collar (54); and a plurality of activation elements in the form of a plurality of activation buttons (56), connected to the switch assembly (40). To this end, the selector collar (54) operatively connects to the selector switch (44) for actuating the selector switch (44), whereas each of the activation buttons (56) operatively connects to the activation switches (46) for respectively actuating the activation switches (46) during use.

With respect to actuating the selector switch (44), the selector collar (54) generally surrounds the elongate body (34) in the form of a ring and may be received within an annular groove (not shown) encircling the elongate body (34). The selector collar (54) similarly encircles the longitudinal axis and is coaxially aligned with the longitudinal axis. In order to select between the at least two predetermined ultrasonic power settings, the selector collar (54) is rotatably mounted against the elongate body (34) and is configured to rotate about the longitudinal axis between a plurality of positions. By way of example, the selector collar (54) rotates among an off position, a maximum position, and a minimum position, which each indicate a unique mode of operating the surgical instrument (14) during the surgical procedure as will be described in greater detail below.

The selector collar (54) and/or the elongate body (34) may further include a plurality of detent features (not shown) configured to urge the selector collar (54) to discrete positions, such as the maximum, minimum, and off positions, in order to inhibit the selector collar (54) from resting in or drifting to an unintended position. Thereby, the operator may more effectively view, select, and retain the angular position of the selector collar (54) relative to the body (34). Detent features may also provide tactile and/or audible feedback indicating that the operator has located selector collar (54) at one of the predetermined angular positions.

The elongate body (34) and the selector collar (54) further include a plurality of indicia (58, 60, 62, 64, 66) configured to indicate to the operator the selected mode of operation unique to the off, maximum, and minimum positions. First, the rotation knob (32) has a "SAFE" indicia (58), a "HI"

indicia (60), and a "LO" indicia (62) angularly positioned thereon. Second, the selector collar (54) includes an indicator arrow (64) projecting distally from the remainder of the selector collar (54) toward the indices (58, 60, 62). As such, rotating the selector collar (54) between the off, maximum, and minimum positions similarly directs the indicator arrow (64) toward the corresponding indicia (58, 60, 62). The selector collar (54) further includes a dual arrow indicia (66) configured to indicate the direction of rotation of the selector collar (54) about the longitudinal axis. While these plurality of indicia (58, 60, 62, 64, 66) show one example for indicating operation of the surgical instrument (18), it will be appreciated that alternative indicia may be used to similarly communicate the intended operation to the operator. As such, these examples are not intended to unnecessarily limit the invention described herein.

With respect to actuating the activation switches (46), the plurality of activation buttons (56) are positioned proximate to the selector collar (54) such that the selector collar (54) and at least one of the activation buttons (56) may be operated simultaneously with one hand of the operator. In the present example, the plurality of activation buttons (56) more particularly includes four activation buttons (56) equally spaced apart from each other and positioned angularly about the elongate body (34). Specifically, the activation buttons (56) shown in FIG. 2 are positioned approximately 90 degrees apart from each other. Each of the activation buttons (56) is biased radially outwardly from the longitudinal axis, but depresses radially inwardly toward the longitudinal axis to actuate the four corresponding activation switches (46) shown in FIG. 3.

It should be understood that the annular arrangement of buttons (56) enables the operator to reach at least one of the activation buttons (56) regardless of where the operator grips the elongate body (34). In other words, the operator will not need to contort their fingers, hand, wrist, or arm in order to activate transducer (21) and blade (20) from whichever angular orientation the operator happens to be grasping handle assembly (24). This enhanced access to buttons (56) may be particularly useful when blade (20) has an asymmetry, such that engaging tissue with different sides of blade (20) (e.g., with blade (20) oriented at different angular orientations about the longitudinal axis of waveguide (22)) will provide different effects on tissue. The operator will thus not be forced to sacrifice ergonomic comfort in order to selectively achieve various orientations of blade (20) relative to tissue.

Buttons (56) may be constructed and operable in accordance with at least some of the teachings of U.S. patent application Ser. No. 14/515,129, entitled "Activation Features for Ultrasonic Surgical Instrument," filed Oct. 15, 2014, issued as U.S. Pat. No. 9,907,565 on Mar. 6, 2018, the disclosure of which is incorporated by reference herein. However, it will be appreciated that alternative button positions may be arranged for such access. Similarly, more or less activation buttons (56) may be used in accordance with the invention described herein, such as three buttons angularly positioned 120 degrees apart from each other.

By selectively moving the selector collar (54) and depressing at least one of the activation buttons (56) shown in FIG. 2, the selector and activation switches (44, 46) are configured to selectively open and close the ultrasonic transducer circuit (42) shown in FIG. 3. To this end, the selector switch (44) is configured to selectively connect to one of a maximum power lead (68), a minimum power lead (70), and an off lead (72). As described herein, the maximum power, minimum power, and off leads (68, 70, 72) respectively correspond to the maximum, minimum, and off positions of the selector collar (54) (see FIG. 2.) In other words, the maximum power lead (68) is configured to define the ultrasonic transducer circuit (42) such that the ultrasonic generator (12) delivers a maximum predetermined power level to the surgical instrument (18) in order to generate a maximum predetermined ultrasonic oscillation. Similarly, the minimum power lead (70) is configured to define the ultrasonic transducer circuit (42) such that the ultrasonic generator (12) delivers a minimum power level to the surgical instrument (18) in order to generate a minimum predetermined ultrasonic oscillation. The off lead (72) conversely opens the ultrasonic transducer circuit (42) in order to inhibit activation of the surgical instrument (18) by preventing electrical power from being delivered from the ultrasonic generator (12) to the ultrasonic transducer (21). In other words, when the selector collar (54) is in the "off" position, pressing buttons (56) will not have any effect. The operator may select such an "off" mode, which may also be referred to as a "safe" mode, in order to inhibit unintended operation of the surgical instrument during the surgical procedure. However, it will be appreciated that alternative modes of operation may be added to or replaced within the switch assembly (40). For example, an alternative example of the actuation assembly (23) and switch assembly (40) may not include the "off" mode features described herein.

In order to further close the ultrasonic transducer circuit (42) for activation, the operator selectively actuates at least one of the four activation switches (46). The exemplary switch assembly (40) of FIG. 3 shows that each of the activation switches (46) is connected in parallel within the switch assembly (40). As such, actuating at least one of the activation switches (46) will selectively close the ultrasonic transducer circuit (42) and direct power in accordance with the selector switch (44). Of course, in the event that the selector switch (44) is open, such as in the "off" mode, then the instrument will not activate, regardless of actuating the activation switches (46). It will be appreciated that the number of activation switches (46) may be augmented to accommodate more or less activation buttons (56) in alternative examples. For example, three activation switches (46) may be used respectively with three activation buttons (56).

In use, the operator manipulates the selector collar (54) as shown in FIGS. 1-2 in order to select the off position or, alternatively, one of the two predetermined ultrasonic power positions in the event that the operator desires to activate the surgical instrument (18). The operator then engages at least one activation button (56) to depress the activation button (56) and selectively activate the transducer (21) to vibrate the blade (20) at the selected ultrasonic power level. Furthermore, the relative positions of the selector collar (54) and activation buttons (56) about the elongate body (34) allow the operator to grip and manipulate the surgical instrument with one hand from effectively any angle during use.

D. Exemplary Alternative Actuation Assemblies

In some instances, it may be desirable to provide a surgical instrument (114, 214) with an alternative form of actuation assembly (123, 223). In particular, it may be desirable to provide the surgical instrument (114, 214) with the actuation assembly (123, 223) that includes a selector collar (154, 254) that translates along the longitudinal axis of an elongate body (134, 234). In addition, it may also be desirable to provide the surgical instrument (114, 214) with the actuation assembly (223) that includes an indicator window (257) for indicating the position of the selector collar (254). Various examples of alternative actuation assemblies are described in greater detail below; while further examples will be apparent to those of ordinary skill in the art in view of the teachings herein. It should be understood that the various actuation assemblies described below may be readily incorporated into the surgical instrument (14) in place of the actuation assembly (23). As such, like numbers described below indicate like features described above.

Figure 4:
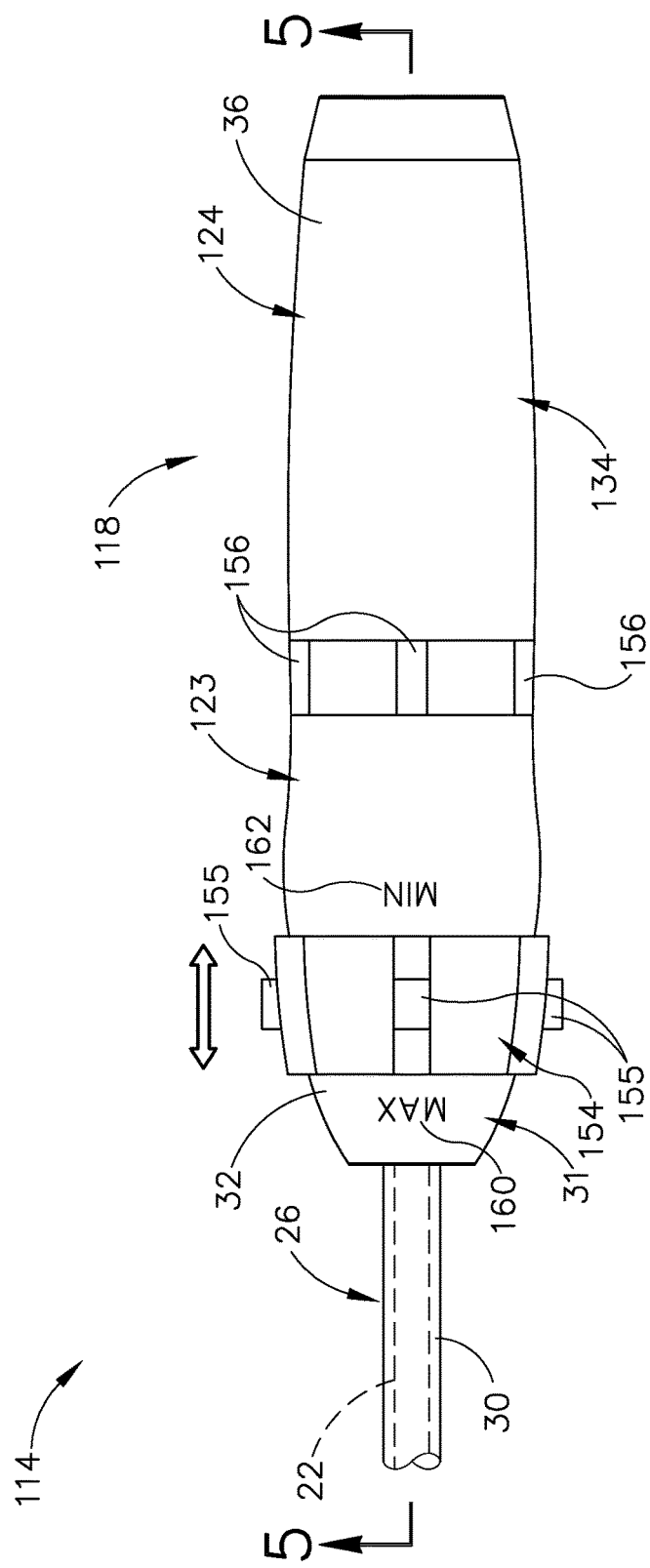
FIG. 4 depicts a top view of a handle assembly of another exemplary surgical instrument.
Figure 5:
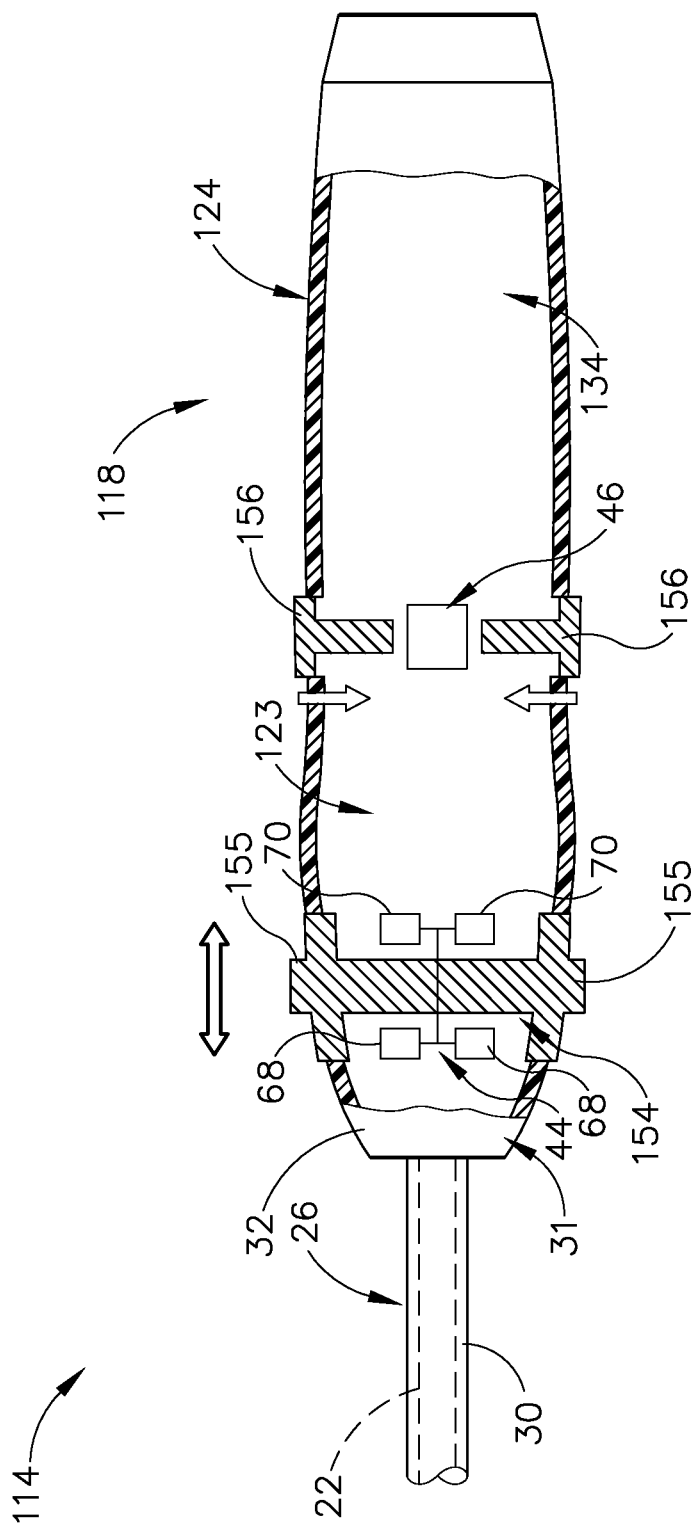
FIG. 5 depicts a cross-sectional view of the surgical instrument of FIG. 4 taken along section line 5-5 of FIG. 4.

1. Exemplary Alternative Actuation Assembly with Distally Positioned Selector Element FIGS. 4-5 show one merely illustrative example of a handpiece (118) and handle assembly (124) having the actuation assembly (123) that connects with the switch assembly (40) (see FIG. 3) for both selecting between at least two predetermined ultrasonic power levels and activating the surgical instrument (114) accordingly. The actuation assembly (123) includes a selector element in the form of a selector collar (154); and a plurality of activation elements in the form of a plurality of activation buttons (156), connected to the switch assembly (40) (see FIG. 3). To this end, as shown in FIG. 5, the selector collar (154) operatively connects to the selector switch (44) for actuating the selector switch (44), whereas each of the activation buttons (156) operatively connects to the activation switches (46) for respectively actuating the activation switches (46) during use.

With respect to actuating the selector switch (44), the selector collar (154) generally surrounds the elongate body (134) in the form of a ring and may be received within an annular groove (not shown) encircling the elongate body (134). The selector collar (154) similarly encircles the longitudinal axis and is coaxially aligned with the longitudinal axis. In order to select between the at least two predetermined power levels of ultrasonic oscillations, the selector collar (154) is translatably mounted against the elongate body (134) and is configured to translate along the longitudinal axis between a plurality of positions. By way of example, the selector collar (154) linearly translates among an off position, a maximum position, and minimum position, which each indicate a unique mode of operating the surgical instrument (114) during the surgical procedure as described above. In addition, a plurality of grip projections (155) extend radially outwardly from the selector collar (154) and are configured to provide additional an additional grip surface for the operator. Of course, any other suitable features may be used on any of the collars described herein, to enhance gripping or other manipulation of such collars, in addition to or in lieu of outwardly protruding features like projections (155).

The selector collar (54) and/or the elongate body (34) may further include a plurality of detent features (not shown) configured to urge the selector collar (154) to discrete positions, such as the maximum, minimum, and off positions, in order to inhibit the selector collar (154) from resting in or drifting to an unintended position. Thereby, the operator may more effectively view, select, and retain the longitudinal position of the selector collar (154) relative to the body (134). Detent features may also provide tactile and/or audible feedback indicating that the operator has located selector collar (154) at one of the predetermined longitudinal positions.

As shown in FIG. 4, the elongate body (134) and the selector collar (154) further include a plurality of indicia (160, 162) configured to indicate to the operator the selected mode of operation unique to the maximum and minimum positions. First, the rotation knob (32) has a distally positioned "MAX" indicia (160) and the elongate body (134) has a proximally positioned "MIN" indicia. As such, linearly translating the selector collar (154) toward the "MAX" indicia (160) will provide selection of the maximum mode of operation, whereas linearly translating the selector collar (154) toward the "MIN" indicia (162) will provide selection of the minimum mode of operation. While these plurality of indicia (160, 162) show one example for indicating operation of the surgical instrument (118), it will be appreciated that alternative indicia may be used to similarly communicate the intended operation to the operator. As such, these examples are not intended to unnecessarily limit the invention described herein.

With respect to actuating the activation switches (46), the plurality of activation buttons (156) are positioned proximate to the selector collar (154) such that the selector collar (154) and at least one of the activation buttons (156) may be operated simultaneously with one hand of the operator. In the present example, the selector collar (156) is positioned distally from the activation buttons (156). The plurality of activation buttons (156) more particularly includes four activation buttons (156) equally spaced apart from each other and positioned angularly about the elongate body (134). Specifically, the activation buttons (156) are positioned approximately 90 degrees apart from each other. Each of the activation buttons (56) is biased radially outwardly from the longitudinal axis, but depresses radially inwardly toward the longitudinal axis to actuate the four corresponding activation switches (46). Thereby, the operator may reach at least one of the activation buttons (156) regardless of where the elongate body (134) is being gripped. However, it will be appreciated that alternative button positions may be arranged for such access. Similarly, more or less activation buttons (156) may used in accordance with the invention described herein, such as three buttons angularly positioned 120 degrees apart from each other.

In use, the operator manipulates the selector collar (154) as shown in FIGS. 4-5 in order to select one of the two predetermined ultrasonic power positions or the off position, which is located between the maximum and minimum positions in the present example. Of course, in order to activate the surgical instrument (118), the operator engages at least one activation button (156) to depress the activation button (156) and selectively activate the transducer (21) to vibrate the blade (20) at the selected ultrasonic power level. Furthermore, the relative positions of the selector collar (154) and activation buttons (156) about the elongate body (134) allow the operator to grip and manipulate the surgical instrument with one hand from effectively any angle during use. Other suitable ways in which the operability of the actuation assembly (123) may be manipulated will be apparent to those of ordinary skill in the art in view of the teachings herein.

Figure 6:
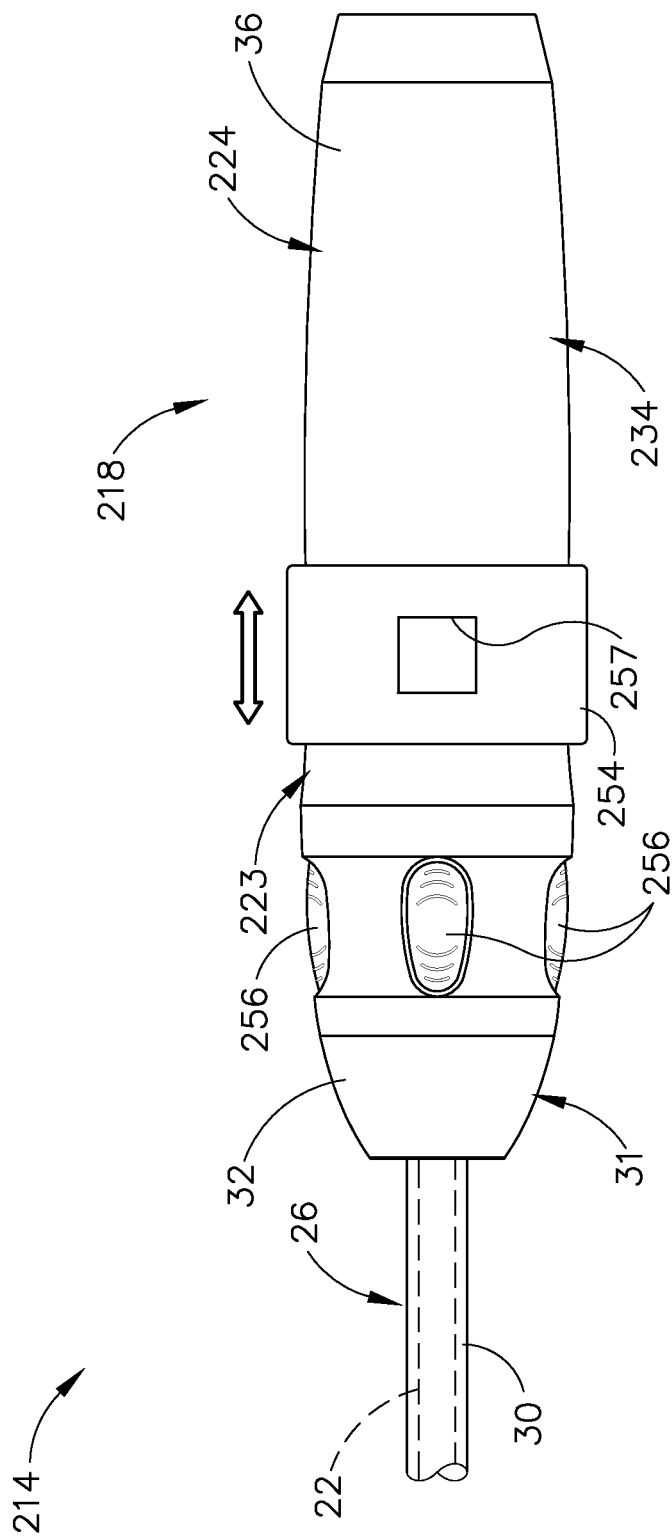
FIG. 6 depicts a top view of a handle assembly of another exemplary surgical instrument.
Figure 7A:
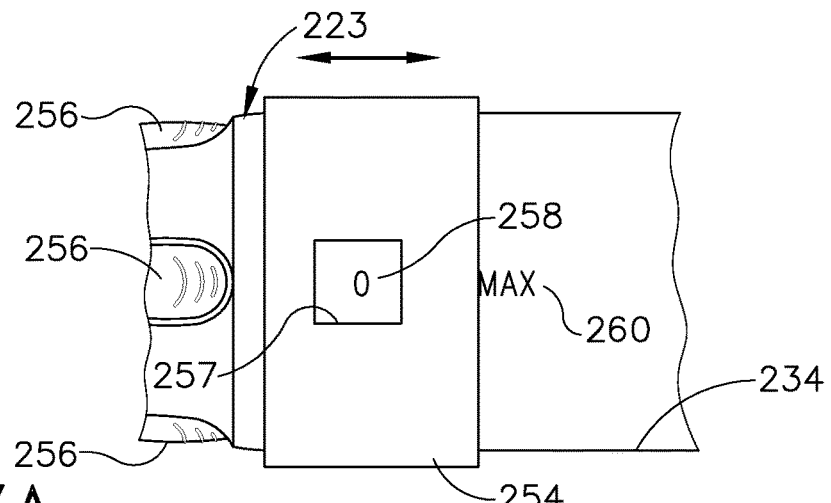
FIG. 7A depicts an enlarged top view of the handle assembly of FIG. 6 having an exemplary selector collar in an off position.
Figure 7B:
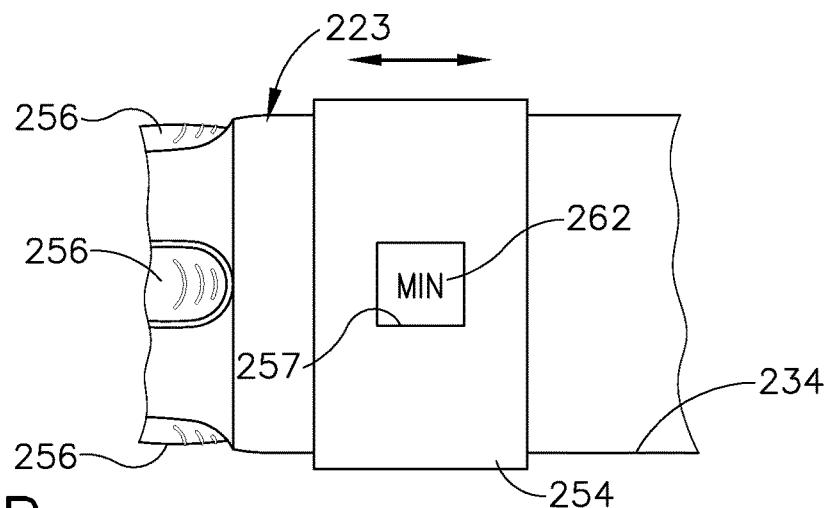
FIG. 7B depicts the handle assembly similar to FIG. 7A, but having the selector collar in a minimum power position.
Figure 7C:
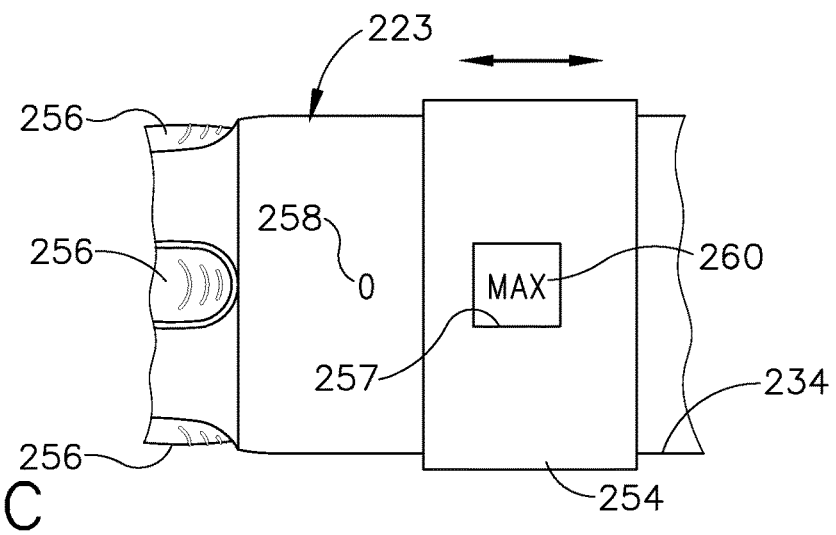
FIG. 7C depicts the handle assembly similar to FIG. 7A, but having the selector collar in a maximum power position.

2. Exemplary Alternative Actuation Assembly with Proximally Positioned Selector Element and Indicator Window FIGS. 6-7C show another merely illustrative example of a handpiece (218) and handle assembly (224) having the actuation assembly (223) that connects with the switch assembly (40) (see FIG. 3) for both selecting between at least two predetermined ultrasonic power levels and activating the surgical instrument (214) accordingly. The actuation assembly (223) includes the selector element in the form of a selector collar (254); and the plurality of activation elements in the form of a plurality of activation buttons (256), connected to the switch assembly (40) (see FIG. 3). To this end, the selector collar (254) operatively connects to the selector switch (44) (see FIG. 3) for actuating the selector switch (44) (see FIG. 3), whereas each of the activation buttons (256) operatively connects to the activation switches (46) (see FIG. 3) for respectively actuating the activation switches (46) (see FIG. 3) during use.

With respect to actuating the selector switch (44) (see FIG. 3), the selector collar (254) generally surrounds the elongate body (234) in the form of a ring and may be received within an annular groove (not shown) encircling the elongate body (234). The selector collar (254) similarly encircles the longitudinal axis and is coaxial with the longitudinal axis. In order to select between the at least two predetermined power levels of ultrasonic oscillations, the selector collar (254) is translatably mounted against the elongate body (234) and is configured to translate along the longitudinal axis between a plurality of positions. By way of example, the selector collar (254) linearly translates among an off position, a maximum position, and a minimum position, which each indicate a unique mode of operating the surgical instrument (114) during the surgical procedure.

The selector collar (254) and/or the elongate body (234) may further include a plurality of detent features (not shown) configured to urge the selector collar (254) to discrete positions, such as the maximum, minimum, and off positions, in order to inhibit the selector collar (254) from resting in or drifting to an unintended position. Thereby, the operator may more effectively view, select, and retain the longitudinal position of the selector collar (254) relative to the body (234). Detent features may also provide tactile and/or audible feedback indicating that the operator has located selector collar (254) at one of the predetermined longitudinal positions.

The selector collar (254) further includes an indicator window (257) configured to align relative to a plurality of indicia (258, 260, 262) that are fixedly positioned on the elongate body (234) to indicate to the operator the selected mode of operation unique to the off, maximum, and minimum positions. The indicator window (257) extends through the selector collar (254) such that selective portions of elongate body (234) are visible to the operator. First, linearly translating the selector collar (254) distally along the elongate body (234) slides the selector collar (254) toward the off position. In turn, an "O" indicia (258) is visible (257) through the indicator window (257) on the elongate body (234). Second, linearly translating the selector collar (254) proximally along the elongate body (234) from the off position (234) next moves the selector collar (254) to the minimum position in order to reveal a "MIN" indicia (262) on the elongate body (234). Third, linearly translating the selector collar (254) even further proximally along the elongate body (234) further moves the selector collar (254) to the maximum position with a "MAX" indicia (260) on the elongate body (234) being visible. In addition, the plurality of indicia (258, 260, 262) are longitudinally aligned on the elongate body (234).

In some versions, some of the indicia (258, 260, 262) may remain visible proximate to the selector collar (254) while not aligned with the indicator window (257). Alternatively, the indicia (258, 260, 262) may be spaced apart from each other along the elongate body (234) with an appropriately sized selector collar (254) such that while one of the indicia (258, 260, 262) is visible through the indicator window (257), the remaining indicia (258, 260, 262) are covered and thereby obscured by the selector collar (254). For example, in the off position, the "O" indicia (258) may be visible, but the "MAX" indicia (260) and the "MIN" indicia (262) may remain covered and thereby obscured from operator view. While these plurality of indicia (258, 260, 262) show one example for indicating operation of the surgical instrument (218), it will be appreciated that alternative indicia may be used to similarly communicate the selected power level or mode to the operator. As such, these examples are not intended to unnecessarily limit the invention described herein.

With respect to actuating the activation switches (46) (see FIG. 3), the plurality of activation buttons (256) are positioned proximate to the selector collar (254) such that the selector collar (254) and at least one of the activation buttons (256) may be operated simultaneously with one hand of the operator. In the present example, the selector collar (256) is positioned proximally from the activation buttons (256). The plurality of activation buttons (256) more particularly includes four activation buttons (256) equally spaced apart from each other and positioned angularly about the elongate body (234). Specifically, the activation buttons (256) are positioned approximately 90 degrees apart from each other. Each of the activation buttons (256) is biased radially outwardly from the longitudinal axis, but depresses radially inwardly toward the longitudinal axis to actuate the four corresponding activation switches (46) (see FIG. 3). Thereby, the operator may reach at least one of the activation buttons (256) regardless of where the elongate body (234) is being gripped. However, it will be appreciated that alternative button positions may be arranged for such access. Similarly, more or less activation buttons (256) may used in accordance with the invention described herein, such as three buttons angularly positioned 120 degrees apart from each other.

In use, the operator manipulates the selector collar (254) as shown in FIGS. 6-7C in order to select one of the two predetermined ultrasonic oscillation positions or the off position, which is located distally from the minimum and maximum positions. Of course, in order to activate the surgical instrument (218), the operator engages at least one activation button (256) to depress the activation button (256) and selectively activate the transducer (21) to vibrate the blade (20) at the selected ultrasonic power level. Furthermore, the relative positions of the selector collar (254) and activation buttons (256) about the elongate body (234) allow the operator to grip and manipulate the surgical instrument with one hand from effectively any angle during use. Other suitable ways in which the operability of the actuation assembly (223) may be manipulated will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument for use during a surgical procedure, comprising: (a) a body defining a longitudinal axis and configured to receive an ultrasonic transducer for selectively generating an ultrasonic oscillation at a first predetermined power level and an ultrasonic oscillation at a second predetermined power level; (b) a shaft assembly projecting from the body, the shaft assembly including an acoustic waveguide configured to communicate the selected first or second predetermined power level therealong; (c) an ultrasonic blade connected to the acoustic waveguide such that the acoustic waveguide communicates the selected first or second predetermined power level to the ultrasonic blade; and (d) an actuation assembly connected to the body and configured to selectively activate the ultrasonic blade, the actuation assembly comprising: (i) a selector collar generally surrounding the body and being selectively moveable relative to the body between a first position and a second position, the selector collar configured to select from the first predetermined power level and the second predetermined power level, and (ii) a plurality of activation buttons operable to initiate activation of the ultrasonic blade at the predetermined power level as selected by the selector collar.

Example 2

The ultrasonic instrument of Example 1, further comprising a plurality of activation switches such that each activation button is configured to respectively actuate one of the plurality of activation switches.

Example 3

The ultrasonic instrument of any one or more of Examples 1 through 2, wherein each of the plurality of activation buttons is disposed angularly about the body proximate to the selector collar and biased radially outwardly from the longitudinal axis, and each of the plurality of activation buttons is configured to depress radially inwardly toward the longitudinal axis.

Example 4

The ultrasonic instrument of any one or more of Examples 1 through 3, wherein the selector collar is selectively rotatable about the longitudinal axis between the first and second positions.

Example 5

The ultrasonic instrument of any one or more of Examples 1 through 4, wherein the selector collar is positioned distally from the plurality of activation buttons.

Example 6

The ultrasonic instrument of any one or more of Examples 1 through 3, wherein the selector collar is selectively translatable along the longitudinal axis between the first and second positions.

Example 7

The ultrasonic instrument of any one or more of Examples 1 through 3 and Example 6, wherein the selector collar is positioned distally from the plurality of activation buttons.

Example 8

The ultrasonic instrument of one or more of Examples 1 through 3 and Example 6, wherein the selector collar is positioned proximally from the plurality of activation buttons.

Example 9

The ultrasonic instrument of any one or more of Examples 1 through 8, further comprising a selector switch operatively connected to the selector collar, wherein the selector collar is movable to selectively actuate the selector switch.

Example 10

The ultrasonic instrument of any one or more of Examples 1 through 9, wherein the selector collar in the first position is configured to provide oscillation of the ultrasonic blade with a low predetermined power level and the selector collar in the second position is configured to provide oscillation of the ultrasonic blade with a high predetermined power level.

Example 11

The ultrasonic instrument of any one or more of Examples 1 through 10, wherein at least one of the body and the selector collar includes a first indicia configured to indicate to an operator when the selector collar is in the first position and a second indicia configured to indicate to the operator when the selector collar is in the second position.

Example 12

The ultrasonic instrument of Example 11, wherein the body includes the first and second indicia and the selector collar includes an indicator arrow extending therefrom, wherein the indicator arrow and the first and second indicia are positioned relative to each other such that the indicator arrow aligns with the selected first or second indicia for indicating to the operator when the selector collar is in the first or second position.

Example 13

The ultrasonic instrument of Example 11, wherein the body includes the first and second indicia and the selector collar includes an indicator window extending therethrough to the body, wherein the indicator window and the first and second indicia are positioned relative to each other such that the indicator window aligns with the selected first or second indicia in order to permit viewing of the selected first or second indicia through the indicator window for indicating to the operator when the selector collar is in the first or second position.

Example 14

The ultrasonic instrument of any one or more of Examples 1 through 13, wherein the selector collar is selectively movable relative to the body between the first position, the second position, and a third position and configured to select respectively between the first predetermined power level, the second predetermined power level, and an off mode, and the off mode inhibits oscillation of the ultrasonic blade despite operation of the activation button.

Example 15

The ultrasonic instrument of Example 14, wherein at least one of the body and selector collar includes a first indicia configured to indicate to an operator when the selector collar is in the first position, a second indicia configured to indicate to the operator when the selector collar is in the second position, and a third indicia configured to indicate to the operator when the selector collar is in the third position.

Example 16

An ultrasonic instrument for use during a surgical procedure, comprising: (a) a body defining a longitudinal axis and configured to receive an ultrasonic transducer for selectively generating an ultrasonic oscillation at a first predetermined power level and an ultrasonic oscillation at a second predetermined power level; (b) a shaft assembly projecting from the body, the shaft assembly including an acoustic waveguide configured to communicate the selected first or second predetermined power level therealong; (c) an ultrasonic blade connected to the acoustic waveguide such that the acoustic waveguide communicates the selected first or second predetermined power level to the ultrasonic blade; and (d) an actuation assembly connected to the body and configured to selectively activate the ultrasonic blade, the actuation assembly comprising: (i) a selector element positioned adjacent to the body and coaxially aligned with the longitudinal axis, the selector element being selectively moveable relative to the body between a first position and a second position, and configured to select from the first predetermined power level and the second predetermined power level, and (ii) at least one activation element positioned adjacent to the body and proximate to the at least one selector element, the at least one activation element operable to initiate activation of the ultrasonic blade at the predetermined power level as selected by the selector element.

Example 17

A method of operating an ultrasonic instrument during a surgical procedure, the ultrasonic instrument having a body, a shaft assembly, an ultrasonic blade, and an actuation assembly, the body defining a longitudinal axis and configured to receive an ultrasonic transducer for selectively generating an ultrasonic oscillation at a first predetermined power level and an ultrasonic oscillation at a second predetermined power level, the shaft assembly projecting from the body, the shaft assembly including an acoustic waveguide configured to communicate the selected first or second predetermined power level therealong, the ultrasonic blade connected to the acoustic waveguide such that the acoustic waveguide communicates the selected first or second predetermined power level to the ultrasonic blade, and the actuation assembly connected to the body and configured to operatively connect to the ultrasonic transducer for selective operation of the ultrasonic blade, the actuation assembly having a selector element and at least one activation element, the selector element positioned adjacent to the body and being selectively moveable relative to the body between a first position and a second position, the at least one activation element positioned adjacent to the body and proximate to the at least one selector element, the method comprising: (a) selecting the first position or the second position for the selector element in order to respectively select the first predetermined power level or the second predetermined power level; and (b) engaging the activation element.

Example 18

The method of Example 17, wherein the selector element is a selector collar that generally surrounds the body and the method further comprises: rotating the selector collar about the longitudinal axis toward at least one of the first and second positions.

Example 19

The method of Example 17, wherein the selector element is a selector collar that generally surrounds the body and the method further comprises: translating the selector collar along the longitudinal axis toward at least one of the first and second positions.

Example 20

The method of any one or more of Examples 17 through 19, wherein the selector element is selectively movable along the body between the first position, the second position, and a third position and configured to select respectively between the first predetermined power level, the second predetermined power level, and an off mode, the method further comprising: selecting the third position for the selector element in order to select the off mode and inhibit oscillation of the ultrasonic blade when the activation element is engaged.

IV. Miscellaneous

While several of the examples described above include contact switches (44, 46), it should be understood that any other suitable kind of switches may be used. Moreover, various other kinds of structures may be used to provide an electrical signal to the generator (12), to close a circuit between the generator (12) and the ultrasonic transducer (21), and/or to otherwise selectively activate the ultrasonic transducer (21) and/or the waveguide (22). Various suitable alternatives will be apparent to those of ordinary skill in the art in view of the teachings herein. It is contemplated that all of these alternatives are included within the meaning of the broad term "switch."

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument for use during a surgical procedure, comprising:
   (a) a body defining a longitudinal axis and configured to receive an ultrasonic transducer for selectively generating an ultrasonic oscillation at a first predetermined power level and an ultrasonic oscillation at a second predetermined power level;
   (b) a shaft assembly projecting from the body, the shaft assembly including an acoustic waveguide configured to communicate the selected first or second predetermined power level therealong;
   (c) an ultrasonic blade connected to the acoustic waveguide such that the acoustic waveguide communicates the selected first or second predetermined power level to the ultrasonic blade; and
   (d) an actuation assembly connected to the body and configured to selectively activate the ultrasonic blade, the actuation assembly comprising:
      (i) a selector collar generally surrounding the body and being selectively moveable relative to the body between a first selector collar position, a second selector collar position, and a third selector collar position, the selector collar configured to select from the first predetermined power level and the second predetermined power level and
      (ii) a plurality of activation buttons operable to initiate activation of the ultrasonic blade at the predetermined power level as selected by the selector collar,
   (e) a switch assembly, including:
      (i) an electrical contact selector switch operatively connected to the selector collar and movable to an open selector position to thereby be configured to electrically disconnect from a transducer circuit, and
      (ii) at least one electrical contact activation switch operatively connected to at least one of the plurality of activation buttons and movable to a closed activation position to thereby be configured to electrically connect to the transducer circuit,
   wherein the electrical contact selector switch in the open selector position is an off mode that inhibits oscillation of the ultrasonic blade despite operation of the at least one activation button directing the at least one electrical contact activation switch to the closed activation position.

2. The ultrasonic instrument of claim 1, wherein each of the plurality of activation buttons is disposed angularly about the body proximate to the selector collar and biased radially outwardly from the longitudinal axis, and each of the plurality of activation buttons is configured to depress radially inwardly toward the longitudinal axis.

3. The ultrasonic instrument of claim 1, wherein the selector collar is selectively rotatable about the longitudinal axis between the first, second, and third selector collar positions.

4. The ultrasonic instrument of claim 3, wherein the selector collar is positioned distally from the plurality of activation buttons.

5. The ultrasonic instrument of claim 1, wherein the selector collar is selectively translatable along the longitudinal axis between the first, second, and third selector collar positions.

6. The ultrasonic instrument of claim 1, wherein the selector collar in the first selector collar position is configured to provide oscillation of the ultrasonic blade with a low predetermined power level and the selector collar in the second selector collar position is configured to provide oscillation of the ultrasonic blade with a high predetermined power level.

7. The ultrasonic instrument of claim 1, wherein at least one of the body and the selector collar includes a first indicia configured to indicate to an operator when the selector collar is in the first selector collar position, a second indicia configured to indicate to the operator when the selector collar is in the second selector collar position, and a third indicia configured to indicate to the operator when the selector collar is in the third selector collar position.

8. The ultrasonic instrument of claim 7, wherein the body includes the first, second, and third indicia and the selector collar includes an indicator arrow extending therefrom, wherein the indicator arrow and the first, second, and third indicia are positioned relative to each other such that the indicator arrow aligns with the selected first, second, or third indicia for indicating to the operator when the selector collar is in the first, second, or third selector collar positions.

9. The ultrasonic instrument of claim 7, wherein the body includes the first, second, and third indicia and the selector collar includes an indicator window extending therethrough to the body, wherein the indicator window and the first, second, and third indicia are positioned relative to each other such that the indicator window aligns with the selected first, second, or third indicia in order to permit viewing of the selected first, second, or third indicia through the indicator window for indicating to the operator when the selector collar is in the first, second, or third selector collar positions.

10. The ultrasonic instrument of claim 1, wherein at least one of the body and selector collar includes a first indicia configured to indicate to an operator when the selector collar is in the first selector collar position, a second indicia configured to indicate to the operator when the selector collar is in the second selector collar position, and a third indicia configured to indicate to the operator when the selector collar is in the third selector collar position.

11. The ultrasonic instrument of claim 1, wherein the electrical contact selector switch is movable between the open selector position, a closed first selector position, and a closed second selector position, wherein the electrical contact selector switch in the closed first and second selector positions are configured to be electrically connected to the transducer circuit, wherein the at least one electrical contact activation switch is movable from an open activation position to the closed activation position, wherein the at least one electrical contact activation switch in the open activation position is configured to be electrically disconnected from the transducer circuit.

12. The ultrasonic instrument of claim 11, wherein the electrical contact selector switch in the closed first or second selector positions in conjunction with the at least one electrical contact activation switch in the closed activation position initiates activation of the ultrasonic blade at the predetermined power level selected by the selector collar.

13. The ultrasonic instrument of claim 12, wherein the electrical contact selector switch and the at least one electrical contact activation switch are electrically connected in series.

14. The ultrasonic instrument of claim 13, wherein the at least one electrical contact activation switch includes a plurality of electrical contact activation switches respectively operatively connected to the plurality of activation buttons, and wherein the plurality of electrical contact activation switches are electrically connected in parallel between the electrical contact selector switch and the transducer circuit.

15. The ultrasonic instrument of claim 1, further comprising a torquing mechanism operatively connected to the waveguide and configured to limit torque applied to the waveguide to a predetermined torque.

16. A method of operating an ultrasonic instrument during a surgical procedure, the ultrasonic instrument having a body, a shaft assembly, an ultrasonic blade, and an actuation assembly, the body defining a longitudinal axis and configured to receive an ultrasonic transducer for selectively generating an ultrasonic oscillation at a first predetermined power level and an ultrasonic oscillation at a second predetermined power level, the shaft assembly projecting from the body, the shaft assembly including an acoustic waveguide configured to communicate the selected first or second predetermined power level therealong, the ultrasonic blade connected to the acoustic waveguide such that the acoustic waveguide communicates the selected first or second predetermined power level to the ultrasonic blade, and the actuation assembly connected to the body and configured to operatively connect to the ultrasonic transducer for selective operation of the ultrasonic blade, the actuation assembly having a selector element and at least one activation element, the selector element positioned adjacent to the body and being selectively moveable relative to the body between a first selector position, a second selector position, and an off mode position, the at least one activation element positioned adjacent to the body and proximate to the selector element, wherein the at least one activation element is selectively movable between a deactivated position and an activated position, the method comprising:
  (a) selecting the first selector position or the second selector position for the selector element in order to respectively select the first predetermined power level or the second predetermined power level and simultaneously selecting the deactivated position thereby inhibiting activation of the ultrasonic blade;
  (b) selecting the first selector position or the second selector position for the selector element in order to respectively select the first predetermined power level or the second predetermined power level and simultaneously selecting the activated position thereby activating the ultrasonic blade in the first predetermined power level or the second predetermined power level, respectively; and
  (c) selecting the off mode position for the selector element in order to inhibit activating oscillation of the ultrasonic blade despite selection of either of the deactivated or activated positions.

17. The method of claim 16, wherein the selector element is a selector collar that generally surrounds the body and the method further comprises rotating the selector collar about the longitudinal axis toward at least one of the first selector position, the second selector position, or the off mode position.

18. The method of claim 16, wherein the selector element is a selector collar that generally surrounds the body and the method further comprises translating the selector collar along the longitudinal axis toward at least one of the first selector position, the second selector position, or the off mode position.

* * * * *